United States Patent
Li et al.

(10) Patent No.: US 9,067,867 B2
(45) Date of Patent: Jun. 30, 2015

(54) PREPARATION OF 5-AMINOSALICYLIC ACID BY GAS PHASE CATALYTIC CARBOXYLATION

(75) Inventors: Guangxing Li, Wuhan (CN); Jinjin Li, Wuhan (CN); Dajian Zhu, Wuhan (CN); Qiang Jiang, Wuhan (CN); Lingli Cai, Linhai (CN); Yong Xie, Linhai (CN); Lixin Gan, Linhai (CN)

(73) Assignees: Zhejiang Huahai Pharmaceutical Co., Ltd., Zhejiang (CN); Huazhong University Of Science And Technology, Wuhan (CN)

( * ) Notice: Subject to any disclaimer, the term of this patent is extended or adjusted under 35 U.S.C. 154(b) by 100 days.

(21) Appl. No.: 13/997,303

(22) PCT Filed: Oct. 20, 2011

(86) PCT No.: PCT/CN2011/081040
§ 371 (c)(1),
(2), (4) Date: Jun. 24, 2013

(87) PCT Pub. No.: WO2012/083753
PCT Pub. Date: Jun. 28, 2012

(65) Prior Publication Data
US 2013/0281730 A1      Oct. 24, 2013

(30) Foreign Application Priority Data
Dec. 25, 2010 (CN) .......................... 2010 1 0622888

(51) Int. Cl.
*C07C 229/64* (2006.01)
*C07C 227/18* (2006.01)
*C07C 227/20* (2006.01)
*C07C 231/12* (2006.01)

(52) U.S. Cl.
CPC ............. *C07C 229/64* (2013.01); *C07C 227/20* (2013.01); *C07C 231/12* (2013.01)

(58) Field of Classification Search
CPC .. C07C 227/00; C07C 227/16; C07C 229/48; C07C 229/36
See application file for complete search history.

(56) References Cited

U.S. PATENT DOCUMENTS 5,616,787 A * 4/1997 Husler et al. .................. 562/423

FOREIGN PATENT DOCUMENTS

| CN | 1053229 A | 7/1991 |
|---|---|---|
| CN | 102126977 A | 7/2011 |
| GB | 706177 A | 3/1954 |
| IN | 200401242 I3 | 6/2006 |
| JP | 63-40600 | 2/1988 |

OTHER PUBLICATIONS

Chen, Yong-Jiang et al., Synthesis of Vinorelbine Tartrate, Chinese Journal of Pharmaceuticals, vol. 30, No. 1, 1999 p. 8-9.
International Search Report dated Feb. 16, 2012 from corresponding International Application No. PCT/CN2011/081040.
Mo, Fenzhu et al., New Method of the Synthesis of Masalazine, Chinese Journal of Pharmaceuticals, vol. 28, No. 8, 1997 p. 341-342.
Yan, Ting-Ren et al., Improve Preparation of Masalazine, Chinese Journal of Pharmaceuticals, vol. 25, No. 12, 1994 p. 539-540.

* cited by examiner

*Primary Examiner* — Rosalynd Keys
*Assistant Examiner* — Jennifer C Sawyer
(74) *Attorney, Agent, or Firm* — Wolf, Greenfield & Sacks, P.C.

(57) ABSTRACT

Disclosed is a process for preparing 5-aminosalicylic acid by gas phase catalytic carboxylation, characterized in that carbon dioxide is introduced into a system of p-acetaminophenol and a basic compound at a temperature of 150° C.~220° C. and a pressure of 0.5~5.0 MPa in the presence of a catalyst, so as to carry out a gas phase catalytic carboxylation reaction to form a 5-aminosalicylate, and the crude product 5-aminosalicylate is separated, and then acidified to prepare 5-aminosalicylic acid (5-ASA). Since the gas phase catalytic reaction replaces a solid phase thermo-chemical reaction, the reaction is significantly improved in terms of the process flow, reaction conditions, product quality and energy consumption. In addition, the reaction has a short reaction time, good selectivity, high yield and no formation of wastes during the reaction, and is suitable for industrial production.

10 Claims, No Drawings

PREPARATION OF 5-AMINOSALICYLIC ACID BY GAS PHASE CATALYTIC CARBOXYLATION

RELATED APPLICATIONS

This application is a national stage filing under 35 U.S.C. §371 of International Application No. PCT/CN2011/081040, filed Oct. 20, 2011, which claims the priority of China Patent Application No. 201010622888.4, filed with the Patent Office of China on 25 Dec. 2010, titled "PREPARATION OF 5-AMINOSALICYLIC ACID BY GAS PHASE CATALYTIC CARBOXYLATION", the contents of which are incorporated herein by reference in its entirety.

FIELD OF THE INVENTION

The present invention relates to a method for the preparation of 5-aminosalicylic acid by a process of gas-solid phase catalytic carboxylation.

BACKGROUND OF THE INVENTION

5-Aminosalicylic acid (5-ASA) is mainly used in industries of medicines, pesticides, etc. Methods for synthesizing 5-ASA currently reported in literatures mainly include four types of process routes: aniline process, salicylic acid method, p-aminophenol carboxylated and p-acetaminophenol carboxylated solid phase synthesis method. They are respectively outlined as follows:

1. Synthetic Process from Aniline

In the patent JP 6340600 disclosed in Japan, the aniline process uses aniline as a starting material to obtain an aniline diazonium salt, which is then coupled with salicylic acid, and then the azo bond is cleaved by reduction to obtain one molecule of 5-ASA while removing another molecule of aniline (see reaction (1) below). Moreover, in another literature (Zhu Zhi-qing et al., Preparation of mesalamine by catalytic hydrogenolysis, Chinese Journal of Pharmaceuticals, 1999, 30(1):8~9), the azo bond is reduced by hydrogen gas using Raney-Ni as catalyst, to obtain 5-ASA (see reaction (2) below), and the yield of this route reported by the literature is no more than 50%. Although the method is easy to operate, it is not suitable for the production because the process route is long, and aniline and azo compounds are toxic, and are environmentally hazardous to some extent, and are easily introduced into the final product by raw materials, thus seriously affect the purity of the product and thereby resulting in increased costs for the purification.

The synthetic route of this process is as follows:

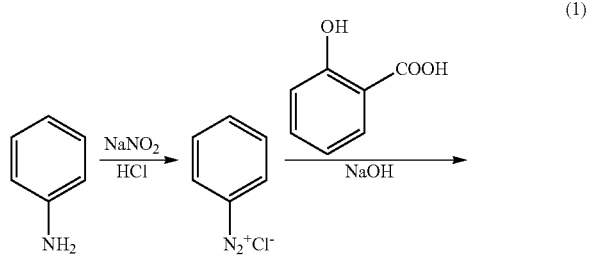

(1)

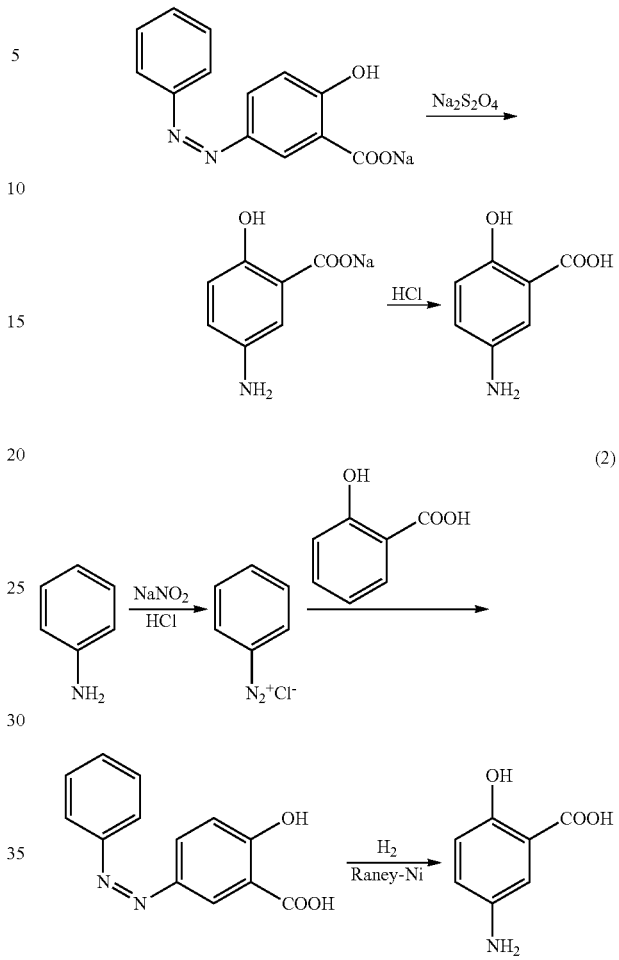

(2)

2. Synthetic Process from Salicylic Acid

The salicylic acid process is disclosed in China Patent Application Publication No.: CN 1053229A and the literature (Yan Ting-ren et al., Improved Preparation of Mesalamine, Chinese Journal of Pharmaceuticals, 1994, 25(14):539~540), in which salicylic acid is used as a starting material and is nitrified by conc. nitric acid to obtain 5-nitrosalicylic acid, and then the nitro group is reduced to an amino group under an acidic condition using iron powder as reducing agent (a preferred condition is hydrochloric acid and iron powder), and 5-ASA is precipitated in a weak acidic condition after treatments (see reaction 3). The total yield of this route is about 50%, and the advantages of this route are that the raw materials are easily available, and the route is simple, so that this route has certain practical values. The disadvantages are that the method suffers from the considerable amount isomers impurity formed by the nitration, which resulted in difficulties for the purification of the product and low yield. Meanwhile, the nitro compounds produced during the Intermediate process are introduced into the final product, so that it is difficult for the amount of nitro compound impurity in 5-ASA product to achieve the requirements for medical applications. In addition, serious environmental pollution will also be caused due to the great amount of nitric acid and iron powder employed in the reactions.

The synthetic route of this process is as follows:

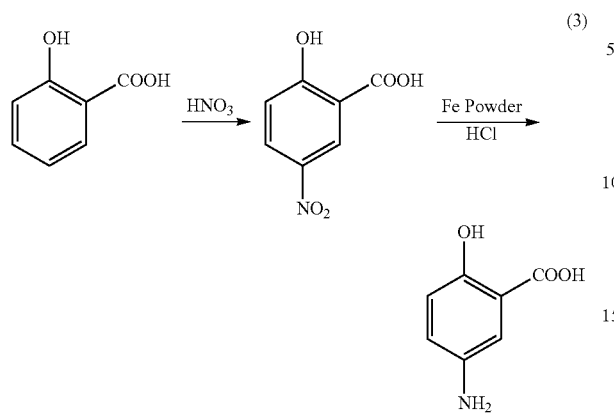

(3)

3. p-Aminophenol Carbon Dioxide Carboxylated Solid Phase Synthesis Method

It is reported by MO Fen Zhu, et al. in "A New Method for Synthesis of Mesalamine that p-aminophenol", Chinese Journal of Pharmaceuticals (1997, 28(8):341~342) that 5-ASA is prepared by reacting p-aminophenol as a starting material with carbon dioxide in a gas phase condition under high pressure and high temperature. This literature simply reports the preparation of 5-ASA by this process and the total yield is over 80%. This process is short in process route, less pollution, and harsh in reaction conditions. However, since the gas-solid carboxylation is performed under high pressure and high temperature, aminophenol is easily oxidized and polymerized. In a addition to the above literature, no any further related patent applications or papers have been published.

The synthetic route of the process of carboxylation of p-aminophenol is as follows:

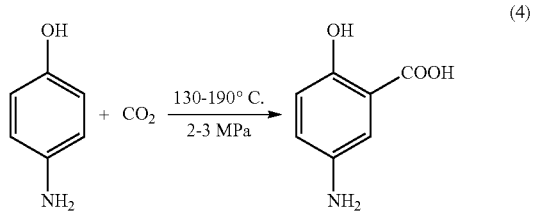

(4)

Conventional synthetic process from aniline or salicylic acid method are still employed in the majority of production processes for 5-aminosalicylic acid, both at home and abroad.

4. Process of Solid Phase Carboxylation of p-Acetaminophenol

It is disclosed in Indian patent IN 2004MU01242 by Kumar et al. that 5-ASA is prepared by performing carboxylation reaction in the presence of a solid base and $CO_2$ under high pressure and high temperature, using p-acetaminophenol as a starting material, but the yield is not reported in this patent. This method has the advantage of simple process and shows certain prospects for industrial applications, but the method reported by this patent is carried out in a condition without a catalyst, thus the reaction rate is slow and the reaction time is as long as 12~24 h. Also, the energy consumption is high and the gas-solid reaction has a poor contact, and is easily overheated locally, causing side reactions such as oxidation and polymerization, resulting in high amount of impurities in the crude product, which is difficult for the purification. So far, no research reports and application examples associated with this process have been found yet.

The synthetic route of this process is as follows:

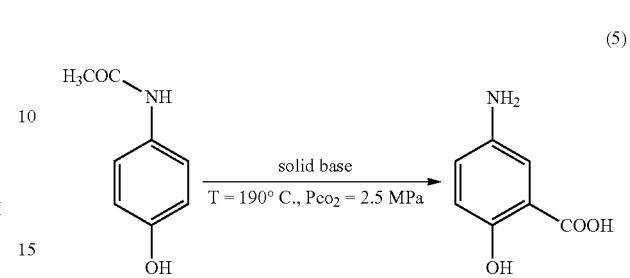

(5)

SUMMARY OF THE INVENTION

The object of the present invention is to provide a process invention for producing 5-aminosalicylate is prepared by gas phase catalytic carboxylation with carbon dioxide in the presence of a catalyst, using the compound of p-acetaminophenol and a basic hydroxide or a carbonate thereof as raw materials, and then acidifying the crude product of 5-aminosalicylate obtained with inorganic acid etc. as raw materials, in which this catalytic process the catalytic reaction instead of solid-phase chemical carboxylation reaction, and it is an object of the present invention in its preferred from to provide a simple, short reaction time, high yield, high product purity process etc. The reaction is also significantly improved in each aspect of process flow, reaction conditions, product quality and reduction in energy consumption.

The object of the present invention is achieved by the following technical measures.

In the present process, carbon dioxide is introduced into a system of p-acetaminophenol and a basic compound under conditions of a temperature of 170° C.~220° C. and a pressure of 0.5~5.0 MPa, in the presence of a catalyst, so as to carry out a gas phase catalytic carboxylation reaction to produce a 5-aminosalicylate, and the crude product of 5-aminosalicylate is separated, and then acidified to prepare 5-aminosalicylic acid.

A class of solid catalysts is screened out in the present invention with good catalytic performance, which is used for carboxylation in gas phase catalysis with good catalytic activities, and the reaction time is short, the reaction yield is high, the selectivity is good so that 5-aminosalicylic acid can be directionally produced, and the catalyst can be easily recovered and recycled. The carboxylation reaction is a gas-solid two-phase reaction and the gas phase catalytic reaction replaces a solid phase thermo-chemical reaction, and the reaction is significantly improved in terms of the process flow, reaction conditions, product quality and energy consumption. Reaction procedures all have sealed circulatory system which produces substantially no pollution, and they are novel methods suitable for industrial continuous production of 5-aminosalicylic acid. The catalyst employed in this reaction is preferably an oxide of silicon, an oxide of aluminum, and an oxide of silicon-aluminum, wherein the oxide of silicon is silicon dioxide, diatomite, and natural quartz sand, the oxide of aluminum is aluminum oxide, and the oxide of silicon-aluminum is silica alumina molecular sieve or aluminum silicate. And the mass ratio of the amount of p-acetaminophenol to the amount of catalyst is 1:0.5~1:10, preferably 1:1~1:3.

The basic compound described in this method can be selected from sodium hydroxide, potassium hydroxide, lithium hydroxide, magnesium hydroxide, calcium hydroxide or the carbonate thereof, wherein the mass ratio of p-acetaminophenol to the basic compound is 1:0.5~1:5, preferably 1:1.5~1:3.

The gas phase catalytic carboxylation reaction is carried out at a pressure of 0.5~5.0 MPa and a temperature of 150° C.~220° C., and it is further preferred that the carboxylation reaction of p-acetaminophenol/the basic compound with carbon dioxide is carried out under a condition of a pressure of 1.5~3.0 MPa and a temperature of 170° C.~200° C., to produce 5-aminosalicylate salt.

The acid employed in the acidification of this process is sulfuric acid, hydrochloric acid, and nitric acid.

The reaction equation of the present invention are as follows:

1. Carboxylation Reaction

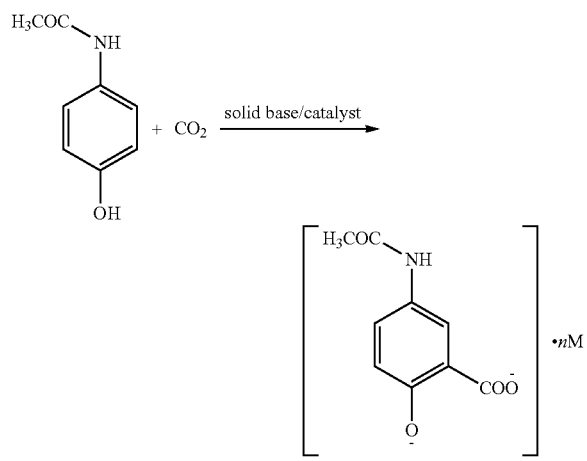

When n=1, M=Ca or Mg divalent metal
When n=2, M=Li, Na or K monovalent metal

2. Acidification Reaction

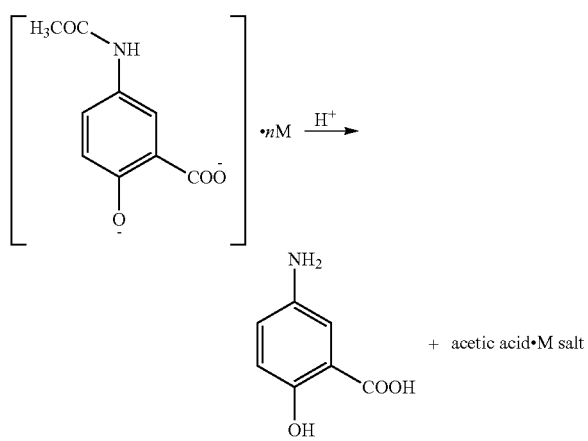

When n=1, M=Ca or Mg divalent metal
When n=2, M=Li, Na or K monovalent metal

The present invention has the following advantages in comparison with the prior art:

(1) The catalyst significantly accelerates the reaction rate under gas phase condition, and the reaction time is 1~4 h.

(2) The catalytic carboxylation reaction should be gas-solid two-phase reaction, and the product yield is up to 95~99%.

(3) The reaction system is a gas-solid system, which is convenient to the treatment processes of adding materials, mixing, and removing materials.

(4) No organic solvent is employed in this reaction system, so that there is substantially no waste pollution.

(5) p-Acetaminophenol-type materials are difficult to be oxidized, thus there are less impurities in crude product, which is convenient for the after treatment and purification.

(6) The reaction selectivity is good and 5-aminosalicylic acid can be directionally produced.

(7) The product has a good quality, less impurity introduced by reacting raw materials, and the purity after purification is up to 99.9%.

(8) This process is simple with safe production and low cost, and is suitable for continuous production in large scale.

DETAILED EMBODIMENTS

To further understand the present invention, preferred embodiments of the present invention are described in conjunction with the examples below. However, it should be understood that these descriptions are only for further illustrating the characteristics and advantages of the present invention, but not limiting the claims of the present invention.

The following specific examples illustrate the effect of the present invention, but the protection scope of the present invention is not limited by the examples below.

Example 1 p-Acetaminophenol 15 g, potassium carbonate 22.5 g, and silicon dioxide 7.5 g were added into a 500 ml autoclave, and $CO_2$ was introduced to perform a carboxylation reaction under a reaction pressure of 1.5 MPa and heated to 170° C., maintained for 4 hours, then the reaction was terminated, cooled to 80° C., and 1500 ml distilled water was added to dissolve potassium 5-aminosalicylate. After decolorization, the aqueous phase was acidified with 20~30% hydrochloric acid until pH=4, cooled and then filtered to obtain the product of 5-aminosalicylic acid, the content is 99.8% and the yield is 88%.

Example 2 p-Acetaminophenol 15 g, sodium hydroxide 37.5 g, and Y-type molecular sieve 15 g were added into a 500 ml autoclave, and $CO_2$ was introduced to perform a carboxylation reaction under a reaction pressure of 2.0 MPa and heated to 180° C., maintained for 3 hours, then the reaction was terminated, cooled to 80° C., and 1500 ml distilled water was added to dissolve sodium 5-aminosalicylate. After decolorization, the aqueous phase was acidified with 20~30% of hydrochloric acid until pH=4, cooled and then filtered to obtain the product of 5-aminosalicylic acid, the content is 99.5% and the yield is 75%.

Example 3 p-Acetaminophenol 15 g, lithium hydroxide 60 g, and aluminum oxide 45 g were added into a 500 ml autoclave, and $CO_2$ was introduced to perform a carboxylation reaction under a reaction pressure of 3.0 MPa and heated to 190° C., maintained for 2 hours, then the reaction was terminated, cooled to 80° C., and 1500 ml distilled water was added to dissolve lithium 5-aminosalicylate. After decolorization, the aqueous phase was acidified with 20~30% hydrochloric acid until pH=4, cooled and then filtered to obtain the product of 5-aminosalicylic acid, the content is 99% and the yield is 85%.

Example 4 p-Acetaminophenol 15 g, calcium carbonate 22.5 g, and quartz sand 67.5 g were added into a 500 ml autoclave, and $CO_2$ was introduced to perform a carboxylation reaction under a reaction pressure of 4.0 MPa and heated to 200° C., maintained for 2 hours, then the reaction was terminated, cooled to 80° C., and 1500 ml distilled water was added to dissolve calcium 5-aminosalicylate. After decolorization, the aqueous phase was acidified with 20~30% hydrochloric acid until pH=4, cooled and then filtered to obtain the product of 5-aminosalicylic acid, the content is 98% and the yield is 90%.

Example 5 p-Acetaminophenol 15 g, potassium hydroxide 37.5 g, and diatomite 90 g were added into a 500 ml autoclave, and $CO_2$ was introduced to perform a carboxylation reaction under a reaction pressure of 5.0 MPa and heated to 210° C., maintained for 1 hour, then the reaction was terminated, cooled to 80° C., and 1500 ml distilled water was added to dissolve potassium 5-aminosalicylate. After decolorization, the aqueous phase was acidified with 20~30% sulfuric acid until pH=4, cooled and then filtered to obtain the product of 5-aminosalicylic acid, the content is 96% and the yield is 92%.

Example 6 p-Acetaminophenol 15 g, calcium carbonate 60 g, and solid catalyst Y-type molecular sieve 7.5 g were added into a 500 ml autoclave, and $CO_2$ was introduced to perform a carboxylation reaction under a reaction pressure of 2.0 MPa and heated to 220° C., maintained for 1 hour, then the reaction was terminated, cooled to 80° C., and 1500 ml distilled water was added to dissolve calcium 5-aminosalicylate. After decolorization, the aqueous phase was acidified with 20~30% hydrochloric acid until pH=4, cooled and then filtered to obtain the product of 5-aminosalicylic acid, the content is 96% and the yield is 85%.

Example 7 p-Acetaminophenol 15 g, sodium hydroxide 22.5 g, and aluminum oxide 15 g were added into a 500 ml autoclave, and $CO_2$ was introduced to perform a carboxylation reaction under a reaction pressure of 3.0 MPa and heated to 170° C., maintained for 3 hours, then the reaction was terminated, cooled to 80° C., and 1500 ml distilled water was added to dissolve sodium 5-aminosalicylate. After decolorization, the aqueous phase was acidified with 20~30% nitric acid until pH=4, cooled and then filtered to obtain the product of 5-aminosalicylic acid, the content is 97% and the yield is 75%.

Example 8 p-Acetaminophenol 15 g, potassium carbonate 37.5 g, and quartz sand 45 g were added into a 500 ml autoclave, and $CO_2$ was introduced to perform a carboxylation reaction under a reaction pressure of 4.0 MPa and heated to 190° C., maintained for 2 hours, then the reaction was terminated, cooled to 80° C., and 1500 ml distilled water was added to dissolve potassium 5-aminosalicylate. After decolorization, the aqueous phase was acidified with 20~30% hydrochloric acid until pH=4, cooled and then filtered to obtain the product of 5-aminosalicylic acid, the content is 99% and the yield is 95%.

Example 9 p-Acetaminophenol 15 g, potassium hydroxide 60 g, and quartz sand 90 g were added into a 500 ml autoclave, and $CO_2$ was introduced to perform a carboxylation reaction under a reaction pressure of 5.0 MPa and heated to 220° C., maintained for 1 hour, then the reaction was terminated, cooled to 80° C., and 1500 ml distilled water was added to dissolve potassium 5-aminosalicylate. After decolorization, the aqueous phase was acidified with 20~30% hydrochloric acid until pH=4, cooled and then filtered to obtain the product of 5-aminosalicylic acid, the content is 97% and the yield is 90%.

Example 10 p-Acetaminophenol 15 g, potassium carbonate 30 g, and aluminum silicate 45 g were added into a 500 ml autoclave, and $CO_2$ was introduced to perform a carboxylation reaction under a reaction pressure of 3.0 MPa and heated to 220° C., maintained for 1 hour, then the reaction was terminated, cooled to 80° C., and 1500 ml distilled water was added to dissolve potassium 5-aminosalicylate. After decolorization, the aqueous phase was acidified with 20~30% hydrochloric acid until pH=4, cooled and then filtered to obtain the product of 5-aminosalicylic acid, the content is 98% and the yield is 90%.

Comparative Example 1 p-Acetaminophenol 15 g, and potassium hydroxide 60 g were added into a 500 ml autoclave, and $CO_2$ was introduced to perform a carboxylation reaction under a reaction pressure of 2.0 MPa and heated to 185° C., maintained for 14 hours, then the reaction was terminated, cooled to 80° C., and 1500 ml distilled water was added to dissolve potassium 5-aminosalicylate. After decolorization, the aqueous phase was acidified with 20~30% hydrochloric acid until pH=4, cooled and then filtered to obtain the product of 5-aminosalicylic acid, the yield is 30%.

Comparative Example 2 p-Acetaminophenol 15 g, and sodium carbonate 60 g were added into a 500 ml autoclave, and $CO_2$ was introduced to perform a carboxylation reaction under a reaction pressure of 2.0 MPa and heated to 185° C., maintained for 24 hours, then the reaction was terminated, cooled to 80° C., and 1500 ml distilled water was added to dissolve sodium 5-aminosalicylate. After decolorization, the aqueous phase was acidified with 20~30% hydrochloric acid until pH=4, cooled and then filtered to obtain the product of 5-aminosalicylic acid, the yield is 10%.

Comparative Example 3 p-Acetaminophenol 15 g, and potassium carbonate 37.5 g were added into a 500 ml autoclave, and $CO_2$ was introduced to perform a carboxylation reaction under a reaction pressure of 3.0 MPa and heated to 185° C., maintained for 14 hours, then the reaction was terminated, cooled to 80° C., and 1500 ml distilled water was added to dissolve potassium 5-aminosalicylate. After decolorization, the aqueous phase was acidified with 20~30% hydrochloric acid until pH=4, cooled and then filtered to obtain the product of 5-aminosalicylic acid, the yield is 35%.

The preparation of 5-aminosalicylic acid by the process of gas phase catalytic carboxylation provided by the present invention has been described by the examples, and a skilled in the art can obviously achieve the technique of the present invention by changing or appropriately modifying and combining the preparation of 5-aminosalicylic acid by the process of gas phase catalytic carboxylation without departing from the content, spirit and scope of the present invention. Specifically, all the similar replacements and changes are obvious to a skilled in the art, and they are all deemed to be within the scope of the present invention.

The invention claimed is:

1. A process for preparing 5-aminosalicylic acid by gas phase catalytic carboxylation, comprising introducing carbon dioxide into a system of p-acetaminophenol and a basic compound in the presence of a catalyst, so as to carry out a gas phase catalytic carboxylation reaction to form a 5-aminosalicylate;
    separating the crude product 5-aminosalicylate; and
    acidifying the crude product to prepare 5-aminosalicylic acid;
    wherein the catalyst is an oxide of silicon, an oxide of aluminum, or an oxide of silicon-aluminum.

2. The process according to claim 1, wherein the oxide of silicon is silicon dioxide, diatomite, or natural quartz sand.

3. The process according to claim 1, wherein the oxide of aluminum is aluminum oxide.

4. The process according to claim 1, wherein the oxide of silicon-aluminum is silica alumina molecular sieve or aluminum silicate.

5. The process according to claim 1, wherein the mass ratio of the amount of p-acetaminophenol to the amount of the catalyst is 1:0.5~1:6.

6. The process according to claim 1, wherein the basic compound is sodium hydroxide, potassium hydroxide, lithium hydroxide, magnesium hydroxide, calcium hydroxide, or the carbonate thereof.

7. The process according to claim 1, wherein the mass ratio of p-acetaminophenol to the amount of the basic compound is 1:1.5~1:4.

8. The process according to claim 1, wherein the gas phase catalytic carboxylation reaction is carried out at a reaction pressure of 0.5~5.0 MPa and a reaction temperature of 150° C.~220° C.

9. The process according to claim 8, wherein the optimized reaction pressure of the process is 1.5~3.0 MPa, and the optimized reaction temperature of the process is 170° C.~22° C.

10. The process according to claim 1, wherein the acid used in the acidification is sulfuric acid, hydrochloric acid, or nitric acid.

* * * * *